United States Patent [19]
Baum

[11] 4,449,522
[45] May 22, 1984

[54] POSITIONING DEVICE FOR USE WITH A TRACHEAL TUBE WHICH IS INSERTABLE INTO A PERSON'S TRACHEA FOR RESPIRATION PURPOSES

[75] Inventor: Marcel Baum, Vienna, Austria

[73] Assignee: Drägerwerk A.G., Fed. Rep. of Germany

[21] Appl. No.: 376,156

[22] Filed: May 7, 1982

[30] Foreign Application Priority Data

May 19, 1981 [DE] Fed. Rep. of Germany ....... 3119854

[51] Int. Cl.³ .......................................... A61M 16/00
[52] U.S. Cl. .......................... 128/200.26; 128/207.15; 604/170; 604/284
[58] Field of Search ...................... 128/207.14, 200.26, 128/207.15, 345, 328; 604/170, 284

[56] References Cited

U.S. PATENT DOCUMENTS

| | | | |
|---|---|---|---|
| 2,463,149 | 3/1949 | Caine | 128/200.26 |
| 2,541,402 | 2/1951 | Caine | 128/200.26 |
| 3,792,701 | 2/1974 | Kloz et al. | 128/328 |
| 3,799,173 | 3/1974 | Kamen | 128/207.15 |
| 3,827,437 | 8/1974 | Inaba | 128/328 |
| 4,244,362 | 1/1981 | Anderson | 128/207.14 |
| 4,289,128 | 9/1981 | Rusch | 128/207.15 |
| 4,309,994 | 1/1982 | Grumwald | 604/284 |
| 4,344,436 | 8/1982 | Kubota | 128/207.15 |

FOREIGN PATENT DOCUMENTS

124593 11/1959 U.S.S.R. ......................... 128/207.14

Primary Examiner—Henry J. Recla

Attorney, Agent, or Firm—McGlew and Tuttle

[57] ABSTRACT

A positioning device for use with a tracheal tube which is insertable into a patient's trachea particularly a tube of a type which includes a respiration gas jet discharge which must be accurately positioned in respect to the first bifurcation of the trachea for optimal respiration effects. The positioning device comprises an elastic measuring probe which is insertable into the tracheal tube and has a distal end which may be projected out of the tube and which carries a carina engaging stop end in the form of outwardly foldable elements which may engage over the top of the carina on engaging the carina in a roof-like manner. The measuring probe includes an opposite end which may be manipulated by a person's hand to regulate the amount of extension of the lower end of the probe beyond the end of the tracheal tube which is inserted into the person's trachea. The elastic measuring probe advantageously carries a pull wire which is connected to the carina engaging stop end and which may be moved in order to unfold the foldable elements of the stop end to cause them to engage over the crown of the bifurcation namely the carina. A measuring sleeve is associated with the elastic measuring probe and when the distal end of the probe is extended out of the tube the sleeve is presented into the end of the tracheal tube which is outside the trachea and the amount of the penetration of the measuring sleeve provides a direct visual reading of the amount of extension of the stop beyond the inserted end of the tracheal tube in the person's trachea.

6 Claims, 2 Drawing Figures

POSITIONING DEVICE FOR USE WITH A TRACHEAL TUBE WHICH IS INSERTABLE INTO A PERSON'S TRACHEA FOR RESPIRATION PURPOSES

FIELD AND BACKGROUND OF THE INVENTION

The invention relates in general to respirating devices and in particular to a new and useful device for positioning a tracheal tube in lengthwise direction in the trachea, in particular for an HFJV (High Frequency Jet Ventilation) tube with at least one jet nozzle.

For ventilation by tube, attention must be paid to correct lengthwise positioning in the trachea. Especially in the case of HFJV the effectiveness of the gas exchange in the lung depends decisively on the position of the jet nozzle in the trachea. It has been found that the distance of the jet nozzle from the first bifurcation (carina) should be about 1.5–2.5 cm for optimum ventilation conditions to be obtained. A tracheal tube with jet nozzles is described in German OS No. 28 47 681.

According to the known state of the art, the position of a tracheal tube and of a jet tube can be determined by radiology or by bronchscopy. Although the jet nozzle clearly appears in the X-ray picture, in many cases the exact position of the carina cannot be established. Besides, frequent repetition of radiology is an unacceptable strain on the patient. Moreover, the results of the radiology are generally not immediately available if high radiation in direct image converter observation is to be dispensed with. With the fiber optics bronchoscope the position of the carina and the distance from the jet nozzles can indeed by determined with sufficient accuracy, but this is a complicated method to be carried out only be skilled personnel. It appears further as disadvantageous that during the examination the bronchoscope takes up almost the entire cross-section of the tube and thus unduly supresses the breathing of the patient who may already have suffered considerable prior damage.

SUMMARY OF THE INVENTION

The invention provides a device for the lengthwise positioning of a tracheal tube, in particular of an HFJV tube in a person's trachea, which permits satisfactory rapid localization without impeding the supply of respiratory air. The essence of the invention is to be seen in that a measuring probe to be pushed forward through the free cross-section of the tube is provided, which has at its distal end a roof-like crown or stop element to be placed on the carina in a roof fashion. With the aid of the probe to be pushed forward through the tracheal tube, the carina can be localized satisfactory by straddling of the stop element, and by appropriate scale division along the probe, or on a measuring sleeve fixable on the probe, a very accurate lengthwise positioning can be effected, in particular for the jet nozzles. During the adjusting process the cross-section of the tracheal tube is sufficiently free, so that ventilation and respirationprocesses are not substantially impeded.

For easy handling of the measuring probe, in particular when pushing it forward through the opening of the tracheal tube, it appears desirable to design the stop element with unfoldable sections, which can be unfolded by an actuating element after passage through the tube and which form a roof type seating surface for straddling the carina.

It may further be advantageous to provide the measuring probe with a displaceable and fixable measuring sleeve, which can be placed on the measuring tube above the proximal end of the tube and which has an appropriate scale division. This scale division makes exact positioning possible. The diameter of the measuring sleeve is expediently selected so that the sleeve can be displaced inside the barrel of the tracheal tube, which is advantageously transparent.

Expediently the measuring probe may consist of x-ray opaque material at least in its distal region of the stop element. Thereby doubts as to the proper seating or unfolding can be eliminated by an X-ray picture.

With the features of the invention, lengthwise positioning of a tracheal tube, in particular of a jet tube, is possible in a short time and without undue hindrance of respiration.

Accordingly, it is an object of the invention to provide an improved positioning device for use with a tracheal tube particularly a tracheal tube having a spiration gas discharge and which includes an elastic measuring probe insertable into the tube and having a stop element therein which is engageable onto the carina which may be manipulated from the exterior end of the tube from which is projects and which advantageously includes a measuring device for measuring the amount of movement of the probe relative to the tracheal tube as an indication of the precise location of the carina within the person's trachea.

A further object of the invention is to provide a respiration device which is simple in design, rugged in construction and and economical to manufacture.

The various features of novelty which characterize the invention are pointed out with particularity in the claims annexed to and forming a part of this disclosure. For a better understanding of the invention, its operating advantages and specific objects attained by its use, reference is made to the accompanying drawings and descriptive matter in which a preferred embodiment of the invention is illustrated.

DESCRIPTION OF THE PREFERRED EMBODIMENT

Figure 1:
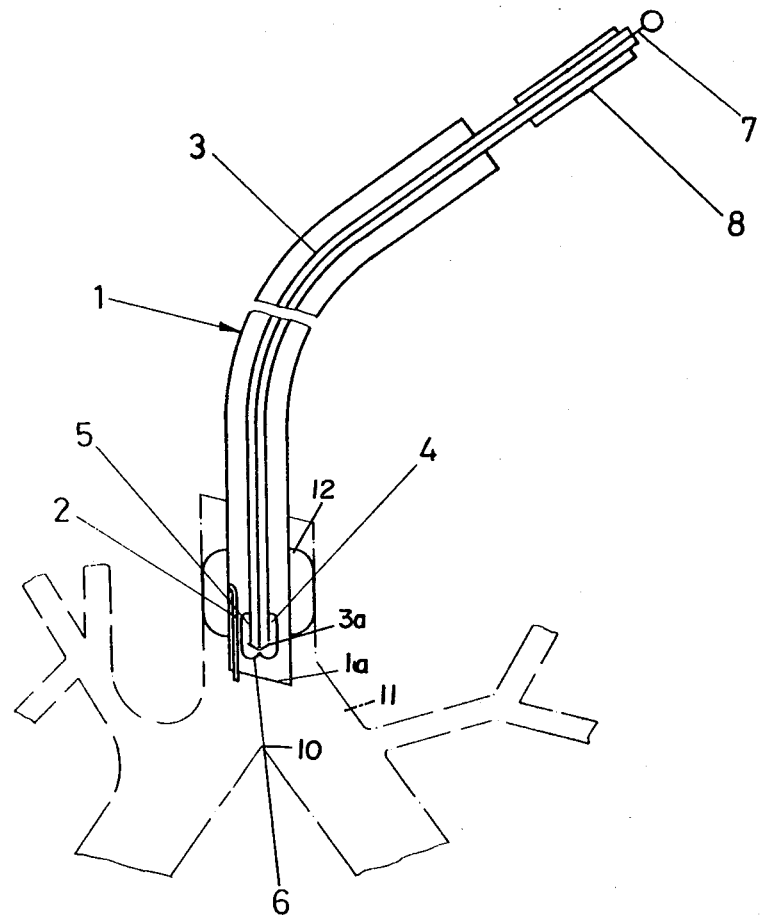
FIG. 1 is a schematic illustration of a tracheal tube having a positioning device constructed in accordance with the invention shown in position in a person's trachea.

Referring to the drawings in particular the invention embodied therein comprises a tracheal tube which, in the embodiment illustrated, is a jet type respiration tube 1 having a distal end 1a which is insertable into a person's trachea indicated 11. The trachea 11 has a major branch bifurcation which has at its center a position or location referred to as the carena. Jet tube 1, for example, is inserted through an incision of the trachea and it is provided with an expandable or flexible sealing member 12 in order to tightly engage the tube in the trachea. In this embodiment the jet tube 1 carries for example in its wall a connecting line for a deflectable jet nozzle 2 which projects slightly out of the distal end and must be centered in respect to the carena 10.

In accordance with the invention a positioning device in the form of an elastic measuring probe 3 is associated with the tracheal tube 1 and it has a distal end 3a which may be maneouvered out of the distal end 1a of the tracheal tube 1 after it is inserted into the trachea by manipulating the outer end of the elastic measuring probe 3. In addition, in accordance with a feature of the invention the distal end 3a of the probe is provided with a carina engageable stop element 6 which may be folded up for manipulation within the tracheal tube 1 as indicated in FIG. 1 or may be expanded as shown in FIG. 2 in order to become centered over the carina in the form of a roof-like crown.

Figure 2:
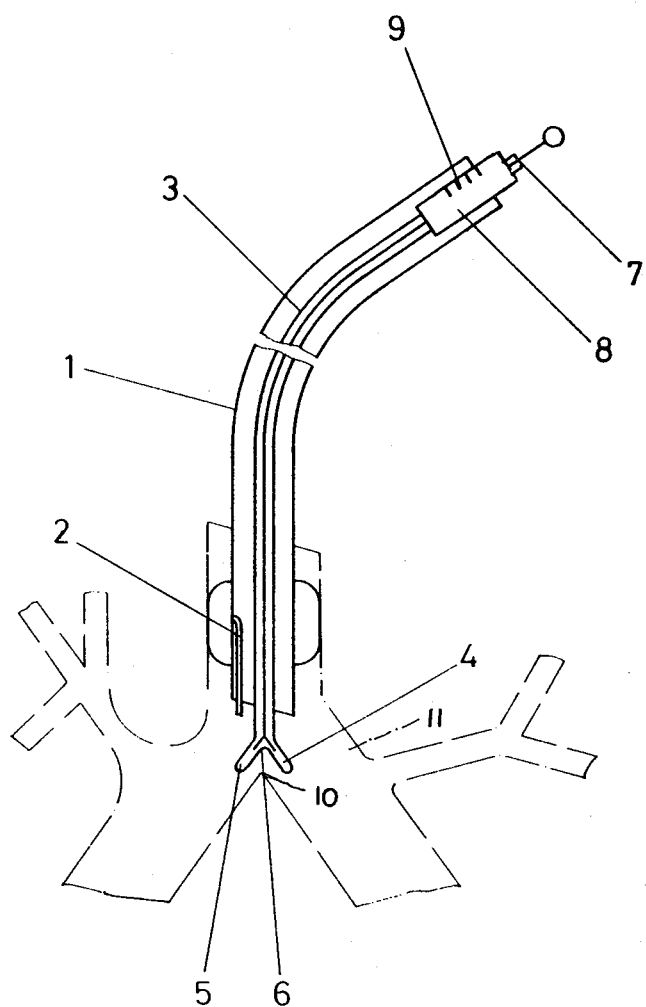
FIG. 2 is a view similar to FIG. 1 showing the measuring probe with its stop element unfolded for engagement over the carena.

In FIG. 1 and 2 the tracheal tube or jet tube 1 can be seen, in the free interior of which the elastically deflectable jet nozzle 2 is arranged. The positioning device contains the elastic measuring probe 3, having the anterior distal end 3a with a stop element 6 made up of two flexible sections or arms 4 and 5 which are spreadable to form a roof-like or inverted V-shaped crown.

The sections 4 and 5 of the stop element 6 are adjustable by an actuator or pull wire 7 guided in the measuring probe 3 between a folded position of small cross-section and a spread position spread in roof fashion.

There is arranged on the measuring probe a measuring sleeve 8 which carries a scale division 9 lying lengthwise. The measuring sleeve 8 is clamped onto the measuring probe 3 in such a way that a given position can be maintained.

FIG. 2 shows the unfolding of the sections 4 and 5 of the stop element 6 and their approximation for straddling the bifurcation center 10 (Carina Tracheae) of the trachea 11.

For positioning the jet nozzle 2 of the jet tube 1, the jet tube is first inserted into the trachae in and upper starting position. The measuring probe 3 is pushed forward with folded sections 4,5 of the stop element 6 through the jet tube 1 while pushing the jet nozzle 2 aside. As the outside diameter of the measuring sleeve 8 is smaller than the free inside diameter of the tracheal tube 1, it can be pushed into the interior thereof. Having passed through the tracheal tube, the sections of the stop element 6 are then unfolded by moving the pull wire 7 having unfolding projections, and the measuring probe is pushed forward until the stop element 6, spread out in roof crown fashion, straddles the carina 10. The measuring sleeve 8 is now inside the jet tube 1. The latter is then pushed forward in the direction of the bifurcation so far that the respective scale division of the measuring sleeve becomes visible at its distal edge. Thus the position of the jet nozzle 2 can be fixed in optimal manner since by observing the scale 9, the amount of projection of the stop element 6 from the bottom of the tube can be shown visually. The measuring probe 3 is then pulled out. If desired, the tube 1 can be provided with a scale continuing upwardly from the lower end which will show the amount of its insertion into the trachea.

While a specific embodiment of the invention has been shown and described in detail to illustrate the application of the principles of the invention, it will be understood that the invention may be embodied otherwise without departing from such principles.

What is claimed is:

1. A positioning device for use with a tracheal tube which is insertable into a person's trachea particularly one of the type having a respirator gas jet discharge which must be positioned relative to a carina of the trachea, comprising an elastic measuring probe adapted to be inserted into the tracheal tube and having a distal end which is adapted to be pushed out of an end of the tracheal tube when the tracheal tube is in the trachea, a carina engaging stop end portion foldably mounted on said distal end of said probe and adapted to be brought into contact with the carina, said measuring probe having an opposite end adapted to extend out of the tube and the person's trachea, said opposite end including means for manipulating said stop end portion so that said distal end can be accurately engaged on the carina, said probe having a length greater than said tracheal tube and at least as great as the length of the trachea from the person's mouth to the carina, said carina engaging stop portion comprising a pair of foldable and unfoldable substantially straight arms, and said manipulating means comprising a connecting member engaged with said arms, extending through said elastic probe and being manipulatable from the outside of the probe at the opposite end thereof to unfold said foldable and unfoldable sections, said foldable arms forming an inverted V-shaped crown for engaging the carina when they are unfolded and being disposed back against said measuring probe when they are folded, and a measuring sleeve mounted on said measuring probe at said opposite end for indicating an amount of projection of said distal end of said probe from the end of the tracheal tube.

2. A positioning device according to claim 1, including a scale associated with said measuring sleeve for measuring the position of said probe relative to the tracheal tube.

3. A positioning device according to claim 1, wherein said carina engaging stop end portion comprises an x-ray opaque material.

4. A positioning device for positioning the distal end of a trachea tube within a trachea at a selected location with respect to a carina of the trachea, comprising:
   a flexible elongated probe (3);
   a pair of arms (4,5) foldably attached to one end of said probe and movable from a folded position lying parallel to and against said one end of said probe, to an unfolded position forming an inverted V-shaped configuration extending beyond said one end of said probe;
   a measuring scale (9) on an opposite end of said probe for indicating the distance between the distal end of a tracheal tube and a carina of a trachea; and
   said probe with measuring scale having a length greater than the tracheal tube and at least as great as a length of a person's trachea from the person's mouth to the carina of the trachea; and
   means associated with said probe and adapted for use when said probe is within a trachea tube for moving said arms to said folded position when said one end of said probe is positioned in the trachea tube, and for moving said arms in said unfolded position when said one end to moved beyond the distal end of the trachea tube to permit engagement of said arms over the carina of the trachea and whereby a desired relative position of the distal end of the tracheal tube can be established with respect to the carina by aligning the proximal end of the tracheal tube with respect to said scale and said scale for the purpose of positioning the trachea.

5. A device according to claim 4, wherein said elongated probe comprises a hollow elastic tube, and said manipulating means comprises a wire (7) having a length greater than said elastic tube extending in said elastic tube;

a pair of unfolding projections connected to an end of said wire in said elastic tube, each unfolding projection extending into one of said arms so that said wire can be manipulated from said opposite end of said elongated probe to move said arms from said folded to said unfolded position.

6. A device according to claim 5, wherein said measuring scale includes a sleeve (8) connected to said opposite end of said elongated probe and carrying said scale.

* * * * *